United States Patent [19]

Ayers

[11] Patent Number: 4,788,491
[45] Date of Patent: Nov. 29, 1988

[54] METHOD OF THE MEASUREMENT OF INTERSTITIAL ATOMS IN ALLOYS INCLUDING THE HYDROGEN CONTENT OF SOLID HYDRIDES, AND OF SORBED SPECIES ON SURFACE

[75] Inventor: William Ayers, Princeton, N.J.

[73] Assignee: Electron Transfer Technologies, Inc., Princeton, N.J.

[21] Appl. No.: 685,414

[22] Filed: Dec. 24, 1984

[51] Int. Cl.$^4$ ............................................. G01N 27/02
[52] U.S. Cl. .................................... 324/71.1; 204/1 T; 204/433; 324/57 R; 324/71.5; 324/158 R
[58] Field of Search ............... 324/439, 442, 445, 425, 324/71.1, 71.5, 57 R, 158 R, 158 D, 233, 232; 204/433, 1 T; 29/574

[56] References Cited

U.S. PATENT DOCUMENTS

| | | | |
|---|---|---|---|
| 2,907,950 | 10/1959 | Raisbeck | 324/57 R |
| 3,290,179 | 12/1966 | Goulding | 324/71.5 X |
| 3,976,377 | 8/1976 | Wu et al. | 324/158 R X |
| 4,240,879 | 12/1980 | Dobson | 204/1 T |
| 4,324,761 | 4/1982 | Harris | 324/71.5 X |
| 4,342,628 | 8/1982 | Buckholz | 324/439 X |
| 4,475,083 | 10/1984 | Linder | 324/233 |

OTHER PUBLICATIONS

Dobson et al., "Some Experimental Factors Which Govern the Potential of the Palladium Hydride Electrode at 25° to 195° C.", vol. 68, 1972, pp. 749–763.
Dobson et al., "Plateau Potentials of the $\alpha+\beta$ Palladium Hydride Electrode at Temperatures Between 25° and 195° C.", vol. 68, 1972, pp. 764–771.
Dodd, Applications of a Phase Sensitive Eddy Current Instrument, 06/64.
Renken et al., Status Report in Eddy Current Theory and Application, 03/83, pp. 24 and 25.

Primary Examiner—Reinhard J. Eisenzopf
Assistant Examiner—Robert W. Mueller
Attorney, Agent, or Firm—Kenneth P. Glynn

[57] ABSTRACT

Disclosed is a method of determining the state of charge and discharge of a host material, e.g., a hydride forming hydrogen storage material, or the interstitial content of an alloy material by the high frequency measurement of the time varying transfer function thereof.

8 Claims, 1 Drawing Sheet

PDH7 R0 = 1.2383 Ω

METHOD OF THE MEASUREMENT OF INTERSTITIAL ATOMS IN ALLOYS INCLUDING THE HYDROGEN CONTENT OF SOLID HYDRIDES, AND OF SORBED SPECIES ON SURFACE

ART TO WHICH THE INVENTION RELATES

The invention relates to alloys where heteroatoms are stored interstitially. The invention especially relates to hydrogen storage devices where hydrogen is stored in the form of a hydride and more particularly to methods of determining the state of charge thereof.

BACKGROUND OF THE INVENTION

Hydrogen storage materials are useful in batteries, fuel cells, superconductors, and chemical reaction systems. More particularly, real time knowledge of the hydrogen content and rate of incorporation of hydrogen into the hydride forming material is essential.

Knowledge of the dynamics of hydrogen absorption and insertion into a hydride forming material is essential for both the rational design of new materials for hydrogen storage applications, and for the optimization of existing hydrogen storage materials. Moreover, knowledge of the state of charge of a hydride based hydrogen storage material is necessary for the efficient, economical operation thereof.

Additionally, the ability to rapidly determine the rate of hydrogen incorporation facilitates the examination of different material compositions to determine their utility as hydrogen storage materials and provides theoretical insight into the electronic interaction of hydrogen with the host lattice.

Direct current measurement of the resistance of metal hydrides has been used to determine the hydrogen content of hydrides ex situ. Alternating current measurements of resistance have been used to measure restructuring, e.g., phase transformations, in disordered metal alloy systems.

SUMMARY OF THE INVENTION

According to the invention herein contemplated both the rate of hydrogen incorporation into a material and state of the amount of hydrogen stored therein may be rapidly determined. It is herein contemplated that the hydrogen content and hydrogen incorporation kinetics are monitored by a high frequency transfer function and/or impedance measurement simultaneous with gaseous and/or electrochemical charging and/or discharging of the hydride.

As herein contemplated the hydride forming, hydrogen storage material is electrochemically charged or discharged with hydrogen under substantially constant current conditions. This produces a constant flux of hydrogen atoms into or out of the hydrogen storage material during the charge and/or discharge process. While the material is undergoing charging or discharging, that is, hydride formation or hydride disassociation, the impedance along the hydride forming material is measured with a phase sensitive detection technique. Alternatively, the hydride forming material may be charged or discharged changing the hydrogen content dr hydrogen partial pressure of a gas in contact with the hydride forming material. The input signal into the hydride forming material is a low amplitude, high frequency signal. The frequency of the test signal is important in determining the depth to which the hydride has penetrated into the hydride forming material. For a specific hydride system there is a minimum threshold frequency required for the herein contemplated method to provide information on the hydride content.

The impedance of the hydride is treated as a parallel impedance of (1) the hydride free material and (2) the hydrided material where the change in resistance with time is a function of the change in volume fraction of hydrited material with time. The change in the hydrided volume is believed to be a function of diffusivity of hydrogen into the material, the solubility of hydrogen in the host material, the rate of hydrogen generation at the surface of the material, and the geometry of the material. The resistivity of the material increases as the hydrogen content of the material increases. The increase in resistivity of the material during charging is substantially reversible. Thus according to the method herein contemplated there is provided an efficient, effective, real time measurement of the state of charge and/or discharge of a hydrogen storage medium and the kinetics of hydrogen charge and/or discharge. The method of the invention is also useful with materials that form interstitial or intercalated alloys by diffusion, e.g., of nickel in tin or alkali metals in graphite, in which the electronic properties of the material are altered by the diffusing component.

The method disclosed herein provides an in-situ measurement of the impedance change during the charging and discharging of the hydride forming material and is believed to rely upon (1) the frequency dependence of the signal in probing the depth or volume fraction of hydride into the host material; (2) the threshold frequency required to detect the time varying change in inpedance of the hydride or interstitial in the host material surrounded by a fluid.

THE FIGURES

The invention may be understood by reference to the figures appended hereto.

DETAILED DESCRIPTION OF THE INVENTION

Figure 1:
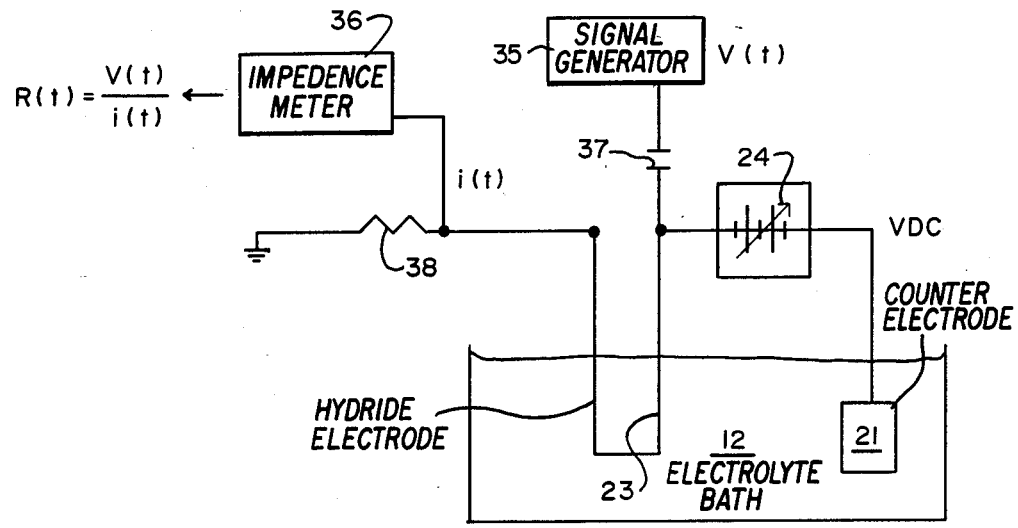
FIG. 1 illustrates electronic instrumentation useful in monitoring the change and impedance along the hydride forming material as well as the associated equipment to electrochemically charge and/or discharge the material.

As herein contemplated, the content of an intersitial or intercalated species, as atomic hydrogen in a hydride forming material, is detected by propagating an electromagnetic impulse along the interface between the host material, e.g., the hydride forming material, and a surrounding fluid, e.g., a hydrogen containing electrolyte or a hydrogen containing gas. It is believed that a strong electronic interaction occurs between the electromagnetic impulse and the inserted, intercalated, or interstitial species and that the concentration of the thusly inserted species is correlated to the change in the transfer function of the electromagnetic impulse. The method may also be used for surface incorporated species, i.e., sorbed species, and hence may function as a sensor of chemical species in a surrounding fluid.

The signal, i.e, the electromagnetic impulse may be any periodic function capable of being transformed by a transfer function, e.g., by digital, analog, Fourier, Fast Fourier, LaPlace, or Z transform techniques, inter alia. The signal may be sinusoidal, a square wave, triangular wave, pulse train, or the like.

The intercalated or interstitial species is atomic rather than molecular and may be hydrogen, rapidly diffusing metals (as Cu, Au, Ag, and Ni), and alkali metals (as Li, Na, or K). The surface incorporated or sorbed species may includes ions, atoms, or molecules.

The host material may be a semiconductor, e.g., chosen from the group consisting of silicon, amorphous silicon, hydrogenated silicon, germanium, amorphous germanium, amorphous hydrogenated germanium, amorphous silicon-germanium alloys, and amorphous silicon-tin alloys. Alternatively, the host material may be lead, tin, indium, thallium, uranium, rare earths, or graphite.

When the incorporated species is hydrogen, the host matrial is a hydride forming material. The hydride forming host material may be chosen from the group consisting of palladium, titanium, tantalum, zirconium, lanthanides, iron, niobium, valandium, and alloys thereof. One particularly desirable group of alloys are the disordered alloys of titanium and nickel, prepared by rapid quench processes. These alloys may also include at least one component chosen from the group consisting of Zr, Al, Sn, In, Pb, the lanthanides, Co, Cr, Cu, Fe, V, Nb, Mg, Mo, Pd, Si, B, C, Hf, and mixtures thereof. One particulary preferred alloy is a Ti-Ni-Al alloy containing from 40 to 75 atomic percent titanium, about 15 to 55 atomic percent nickel, and up to about 15 atomic percent aluminum.

According to the invention described herein there is provided method and apparatus for the rapid, direct, real time monitoring of the rate of hydrogen incorporation into a hydrogen storage material. As herein contemplated the method utilizes an electromagnetic impulse, for example, a high frequency impulse, impedance measurement of the alloy forming material, e.g., the hydride forming material, to monitor the kinetics of addition of interstitial or intercated atom insertion, e.g., hydrogen insertion and hydride formation, during and simultaneous with insertion, e.g., either charging or discharging of the hydride forming material, e.g., by gaseous or electrochemical charging and discharging of the material.

As herein contemplated the hydride storage material is charged, e.g., gaseously charged and/or electrochemically charged, and/or discharged, e.g., gaseously discharged and/or electrochemically discharged, with hydrogen under substantially constant conditions, e.g., constant current conditions or with constant hydrogen content at the boundry between the hydride forming phase and the surrounding fluid. This produces a constant flux of hydrogen atoms, in units of either moles or atoms per unit area per unit time, for example moles per square per centimeter per second, or atoms per square per centimeter per second, into or out of the hydride forming material during the charge and/or discharge stage.

While the hydride forming material is undergoing charging and/or discharging, the impedance along the hydride forming material is measured with high frequency, low voltage detection techniques herein contemplated. The input signal into the hydride forming material has an amplitude of from about 1 millivolts to about 1000 millivolts, and preferably from about 8 to about 12 millivolts, and a frequency of from about 1000 hertz to about 100 megahertz and especially from about 50,000 hertz to about 500,000 hertz. The frequency of the test signal determines the depth to which the hydride has penetrated into the hydride forming material.

The conductivity of interstitial alloys such as hydrides is believed to be controlled by the density of electonic states at the Fermi level. As interstitials are added or removed from the host material, electrons from the interstitials are donated or removed from the host Fermi level. This moves the Fermi level along the density of electronic states function of the host such that the number of electrons available to carry an electomagnetic wave is increased or decreased. Hence, if a material has a density of states that decreases with increasing Fermi level, the conductivity will decrease. Conversely, if the density of states increases with increasing Fermi level, the conductivity will increase.

It has been found that electromagnetic waves of sufficient frequency and amplitude interact strongly with the electronic changes in the material brought on by the interstital diffusion into the host material. As herein contemplated, the concentration of intersitial can be determined by a transfer function or impedance measurement using such electromagnetic waves.

The depth to which the intersititial has entered the host can also be determined by changing the frequency of the electromagnetic wave. This is believed to be due to the fact that electromagnetic waves propagating along a substantially conducting medium penetrate into the medium to a depth known as the skin depth. This depth of penetration is described by the equation (1):

$$\text{Delta} = [2/(\text{Omega})(\text{Sigma})(\text{Mu})]^{0.5} \qquad (1)$$

where
delta is the depth of penetration,
omega is the frequency of the electromagnetic wave,
sigma is the conductivity of the medium, and
mu is the electronic permeability of the medium.

Thus the depth of penetration decreases with the square root of an increase in frequency. For example, in nickel, a hydride forming material, the skin depth is 4.4 millimeters at 1000 hertz and 0.014 millimeters at 1 million hertz.

According to the invention herein contemplated the impedance of the hydride is modeled as a parallel impedance of the hydride free material and the hydride saturated material. The total resistance of the two components in parallel is given by equation (2):

$$1/R = (G_p A_p + G_h A_h)/L \qquad (2)$$

where
L is the length of the material to be charged with hydrogen;
$A_h$ is the cross sectional area of the material that is in the hydride form;
$A_p$ is the cross sectional area of material that is in the non-hydride form;
$G_h$ is the conductivity of the hydride material; and
$G_p$ is the conductivity of the non-hydrided material.

The normalized resistance change is given by equation (3):

$$(R - R_o)/R_o = G_p A_o/(G_p A_p + G_p A_h) - 1 \quad (3)$$

where
$A_o$ equals $A_h + A_p$ and is the total cross-sectional area of the material; and
$R_o$ equals $G_p A_o/1$.

The conductivity G is defined as an equation (4):

$$G = e \, m \, N \quad (4)$$

where
e is the electronic charge;
m is the mobility of the electrons in the material; and
N is the density of states at the fermi level.

The electronic mobility in the hydrided and non-hydrided states are substantially equal, whereby equation (3) becomes equation (5);

$$[R(t) - R_o]/R_o = [1 + (A_h(t)/A_o)(N_p + N_h)/N_p]^{-1} \quad (5)$$

where
t indicates time,
$N_p$ indicates non-hydrided material, and
$N_h$ indicates hydrided material.

The change in hydrided area is a function of the diffusivity of hydrogen into the material, the solubility of hydrogen in the material, the rate of hydrogen generation at the surface of the material and the geometry of the material.

A simple approximate solution for the hydrided area is given by equation (6):

$$A_h(t) = k \, D_h \, t \quad (6)$$

where
$D_h$ equals the diffusivity of hydrogen in the material;
K equals a constant proportional material to geometry and surface hydrogen generation rate; and
t equals time in seconds.

Rearranging equations (5) and (6) yields equation (7):

$$(R(t) - R_o)/R_o = [1 + (k \, D_h \, t/A_o)(N_p + N_h)/N_p]^{-1} - 1 \quad (7)$$

Equation (7) describes the increase in resistance during charging with hydride to the hydride saturation level of the material.

Apparatus for charging and/or discharging hydrogen, with simultaneous measurement of the state of charge is shown in FIG. 1. The apparatus 1 shown in FIG. 1 includes a electrolyte bath 12 having a metal counter electrode 21 and a hydride electrode, e.g., wire 23, in the electrolyte. A dc power supply is used for charging and/or discharging the electrode 23. In this way hydride is formed or disassociated at the electrode 23. An ac signal generator 35 provides a sine wave signal, for example a signal of about 1 to about 1000 milli-volts and about 1 kilohertz to about 10 megahertz to the hydride electrode 23 through a coupling capacitor 37, for example a 100 picofarad capacitor. The phase and amplitude signal is read through an ac impedance meter 36 and a measuring resistor 38. The output of the ac impedance meter yields the instantaneous resistance R(t) of equations 4 and 6. The value of R(t) can be inserted in an appropriate nomograph, table, or personal computer whereby to yield the instantaneous state of charge of the hydride type hydrogen storage material.

The invention may further be understood by reference to the following example.

A 0.01 inch diameter by 3 inch long palladium wire was utilized as the electrode during charging and discharging of the palladium wire with hydrogen. The instantaneous conductivity of the wire was measured utilizing the device shown in FIG. 1 where the electrolyte bath was 1 normal sulphuric acid. The dc power supply was a 6 volt, 50 milliamp constant power supply. The ac signal generator with a 0.1 volt, 100 killohertz generator, the ac impedance meter was a a Hewlett-Packard Model 4274A. The resistivity of the palladium wire increased as the hydrogen content thereof increased. The increase in resistivity of the palladium wire during charging appeared to be reversible. The results of the test are shown in FIG. 2.

This ability to monitor the hydride content through the impedance in the palladium/palladium hydride system in the above electrolyte is only observed at frequencies greater than about 100 kilohertz. At lower frequencies no change in impedance is observed.

Figure 2:
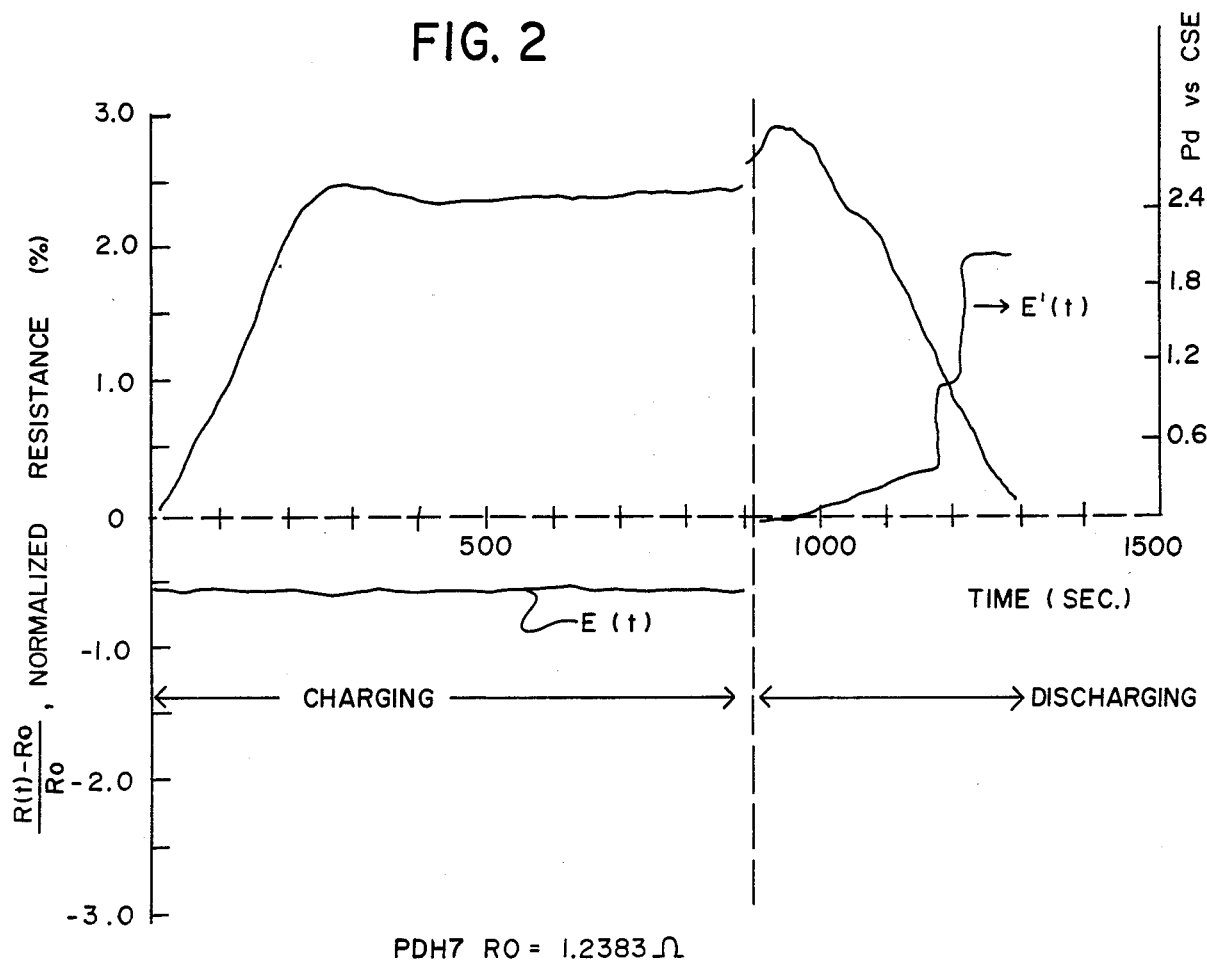
FIG. 2 is a representation of experimental data for the change in normalized resistance of a palladium wire during the charging of the palladium with hydrogen to form palladium hydride and discharging of the palladium wire to disassociate the hydride and release hydrogen in accordance with Example 1.

FIG. 2 shows resistance versus time at constant hydrogen charging or discharging current. In the charging section the normalized resistance increases sharply to a constant level and thereafter remains constant. In the discharge section the normalized resistance decreases to its original level as hydrogen is removed from the material. Measurement of the quantity of hydrogen extracted during discharge shows that the palladium is saturated with hydride at about 400 seconds into the charging period. The palladium resistance increased about 2.5% during the hydride charging period. Discharging was seen to be essentially completely reversible. The linear increase and decrease in the normalized resistance with time is in agreement with the physical model summarized by equation (7).

The discontinuity or hump in the normalized resistance curve at the beginning of the discharge section of FIG. 2 is believed to be related to the rate of phase transformation of hydrided to non-hydrided material within the palladium wire. The size of the discontinuity is dependent on the rate of charging and discharging. Hence the method can also provide information on the kinetics of phase transformation in interstitial alloys.

The second curve in FIG. 2, labeled E'(t) shows the change in the electochemical potential of the hydride forming material (versus a reference electrode) during the charge and discharge steps. Monitoring E'(t) is a known technique for detecting hydrogen adsorbed on the surface of hydrides. Only during discharge is any information on the hydrogen surface coverage of the material discernable. As seen in FIG. 2 during the charging stage, the value of E'(t) remains constant indicating that the surface of the material is fully covered, but providing no information of the hydrogen content below the surface. Only during the discharge stage is any information on the hydrogen surface coverage discernable. However, not a direct correlation can be made between E'(t) and hydrogen content below the surface of the hydride.

In contrast to the voltage measurement of E(t) the herein contemplated impedance measurement along the hydride material clearly shows in FIG. 2 the increase and decrease of hydrogen in the hydride phase during the charging and discharging steps.

The method of the invention provides an in situ to method to measure the formation of a solid hydride. The method is further useful for rapid screening or testing of new materials, such as disordered materials for hydrogen storage and other hydride applications.

The method of the invention is useful to monitor the state of charge of electrochemical hydrogen storage batteries, gaseous hydrogen storage batteries and the bulk hydride storage of hydrogen. The method of the invention may also be used to monitor the rate of diffusion of interstitial or intercalated atoms during the formation of alloys.

While the invention has been described with respect to certain preferred exemplifications and embodiments thereof, it is not intended to limit the scope of the invention thereby but solely by the claims appended thereto.

I claim:

1. A method of detecting the concentration and depth of incorporated mobile atoms into a host material from a surface of the host material, wherein the host material is surrounded by a conducting electrolyte fluid, and the incorporated mobile atoms have diffused through and electronically interacted with said host material, which comprises:
   (a) propagating a variable frequency, periodic, electromagnetic signal along an axis of the host material;
   (b) calculating the depth of penetration of the signal at a fixed frequency, according to the following formula:

Depth of Penetration = (2/(frequency of electromagnetic signal)(conductivity of host material)(electronic permeability of host material))$^{0.5}$;

(c) stepping the frequency of the electromagnetic signal to change the depth of penetration of the signal;
   (d) detecting impedence components of the electromagnetic signal at it enters and leaves the host materials; and,
   (e) calculating the volume fraction of incorporated mobile atoms at a specific depth based on the impedence data for each frequency as a function of the penetration depth of the signal at each frequency.

2. The method of claim 1 wherein the electromagnetic signal is chosen from the group consisting of sinusoidal, square wave, triangular wave, and impulse train signals.

3. The method of claim 1 wherein the electromagnetic signal has a frequency of about 100 hertz to about 100 megahertz and has an amplitude of about 1 millivolt to about 100 millivolts.

4. The method of claim 1 wherein the incorporated species is atomic hydrogen and the host material is a hydride forming material.

5. The method of claim 1 wherein the host material is an electrically conductive material chosen from the group Pd, Ti, Ta, Zr, La, Fe, Nb, V, and alloys of PdFe, PdTi, PdV, PdLa, PdZr, LaNi, LaFe, and LaNiFe.

6. The method of claim 5 wherein the host material is a titanium-nickel alloy comprising at least one element selected from the group consisting of zirconium, aluminum, tin, indium, lead, rare earth metals, cobalt, chromium, copper, iron, vanadium, niobium, magnesium, molybdenum, palladium, boron, carbon, and hafnium.

7. The method of claim 6 wherein the titanium-nickel alloy comprises:
   about 40 atomic percent to about 75 atomic percent of titanium;
   about 15 atomic percent to about 55 atomic percent of nickel; and,
   up to about 15 atomic percent to aluminum.

8. The method of claim 1 wherein the incorporated species is selected from the group consisting of atomic hydrogen and the alkali metals.

* * * * *